(12) United States Patent
Tanaka (10) Patent No.: US 8,211,132 B2
(45) Date of Patent: Jul. 3, 2012

(54) ULTRASONIC SURGICAL APPARATUS

(75) Inventor: Kazue Tanaka, Sagamihara (JP)

(73) Assignee: Olympus Corporation, Tokyo (JP)

( * ) Notice: Subject to any disclaimer, the term of this patent is extended or adjusted under 35 U.S.C. 154(b) by 2025 days.

(21) Appl. No.: 10/858,181

(22) Filed: Jun. 1, 2004

(65) Prior Publication Data

US 2004/0249318 A1 Dec. 9, 2004

(30) Foreign Application Priority Data

Jun. 6, 2003 (JP) .................................. 2003-162840

(51) Int. Cl.
*A61B 17/32* (2006.01)
(52) U.S. Cl. .............................. 606/169; 601/2; 600/437
(58) Field of Classification Search .................. 606/169; 601/2; 600/437
See application file for complete search history.

(56) References Cited

U.S. PATENT DOCUMENTS

| | | | | |
|---|---|---|---|---|
| 3,041,872 A | * | 7/1962 | Rankin et al. .................... | 73/612 |
| 5,431,664 A | * | 7/1995 | Ureche et al. ................. | 606/128 |
| 6,183,426 B1 | * | 2/2001 | Akisada et al. ................... | 601/2 |
| 6,261,235 B1 | * | 7/2001 | Amano et al. ................. | 600/485 |
| 2002/0043108 A1 | * | 4/2002 | Schafer et al. .................. | 73/632 |
| 2002/0052616 A1 | | 5/2002 | Wiener et al. | |

FOREIGN PATENT DOCUMENTS

| | | |
|---|---|---|
| JP | 2000-271140 | 10/2000 |
| JP | 2002-078716 | 3/2002 |
| JP | 2003-153919 | 5/2003 |

* cited by examiner

*Primary Examiner* — Ryan Severson
*Assistant Examiner* — Julie A Szpira
(74) *Attorney, Agent, or Firm* — Scully, Scott, Murphy & Presser, P.C.

(57) ABSTRACT

A probe is connected to an ultrasonic vibrator and can transmit ultrasonic vibrations to a living body tissue. A PLL circuit can generate a drive signal for driving the ultrasonic vibrator. A P-value detecting circuit detects a voltage peak value and current peak value of the drive signal to be supplied from the PLL circuit to the ultrasonic vibrator. A standardizing circuit standardizes voltage information and current information of the drive signal based on a result of the P-value detecting circuit. A comparing circuit is a comparing unit for comparing voltage information standardized by the standardizing circuit and current information standardized by the standardizing circuit. A CPU identifies an abnormality of the probe based on a comparison result of the comparing circuit.

5 Claims, 7 Drawing Sheets

ULTRASONIC SURGICAL APPARATUS

This application claims benefit of Japanese Application No. 2003-162840 filed on Jun. 6, 2003, the contents of which are incorporated by this reference.

BACKGROUND OF THE INVENTION

1. Field of the Invention

The present invention relates to an ultrasonic surgical apparatus for transmitting ultrasonic vibrations from an ultrasonic vibrator to a living body tissue through a probe.

2. Description of the Related Art

Conventionally, a variety of apparatuses for outputting ultrasonic vibrations by using an ultrasonic converter have been in actual use. For example, a surgical ultrasonic knife and an ultrasonic processor are known.

Especially, a surgical ultrasonic knife has an ultrasonic vibrator stored in a case and a probe connecting to the ultrasonic vibrator. The surgical ultrasonic knife transmits ultrasonic vibrations from the ultrasonic vibrator to a living body tissue through the probe.

For such a conventional surgical ultrasonic knife, a variety of technologies relating to detection of water leaks into the case, for example, have been proposed. However, the same methods cannot be simply used for detecting abnormalities occurring in the probe.

In order to handle this problem, a conventional ultrasonic surgical apparatus disclosed in Japanese Unexamined Patent Application Publication No. 2000-271140, for example, has a function for feeding weak current through a probe and monitoring the impedance in order to check the detection of an abnormality in the probe.

SUMMARY OF THE INVENTION

An ultrasonic surgical apparatus includes an ultrasonic vibrator which can generate ultrasonic vibrations, a probe which is connected to the ultrasonic vibrator and can transmit the ultrasonic vibrations, drive signal generating means which can generate a drive signal for driving the ultrasonic vibrator, drive signal distortion detecting means which can detect a waveform distortion of the drive signal to be supplied from the drive signal generating means to the ultrasonic vibrator, and probe abnormality identifying means for identifying an abnormality of the probe based on a detection result of the drive signal distortion detecting means.

DETAILED DESCRIPTION OF THE PREFERRED EMBODIMENTS

Embodiments of the present invention will be described below with reference to drawings.

First Embodiment

Figure 1:
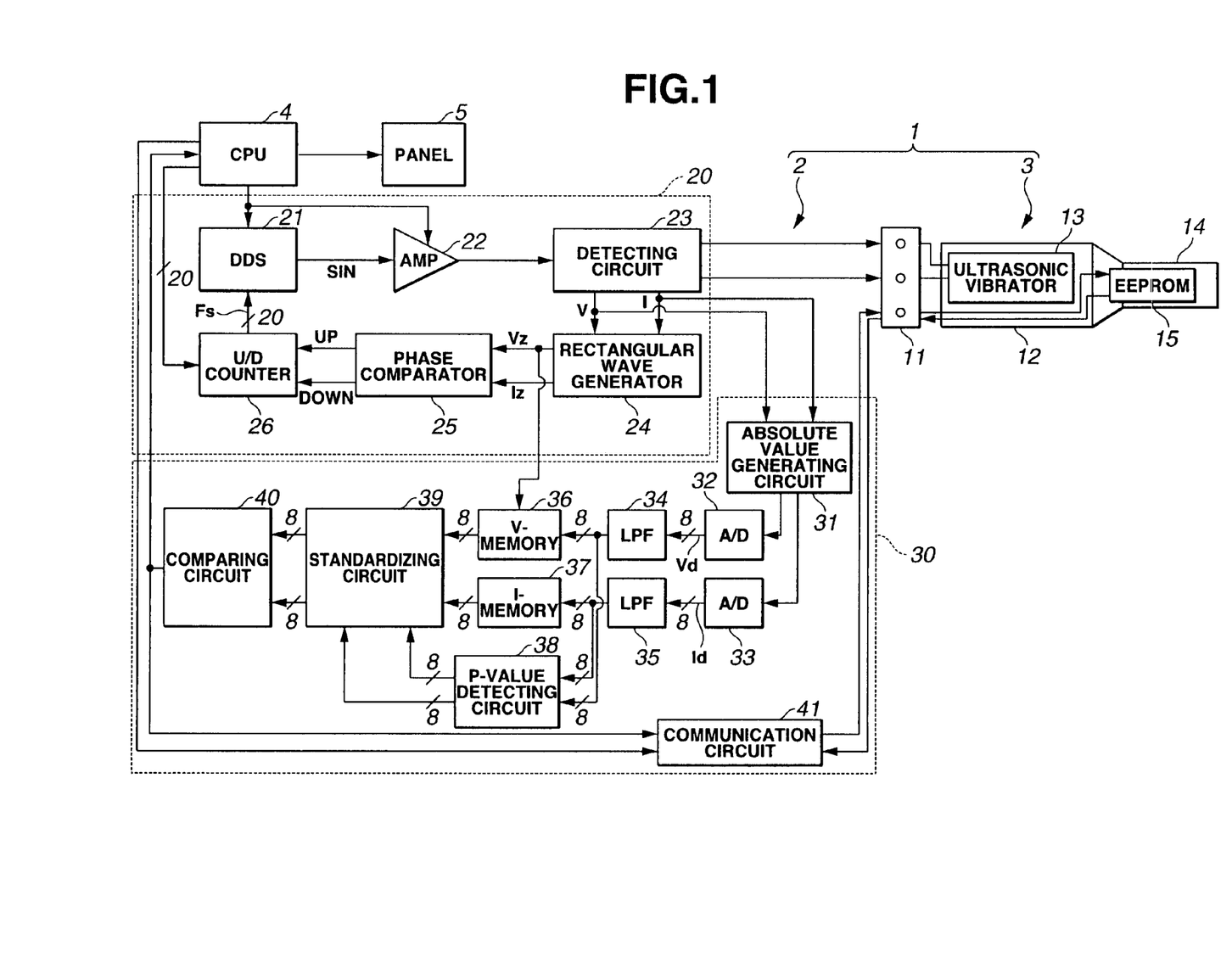
FIG. 1 is a block diagram showing a configuration of an ultrasonic surgical apparatus according to a first embodiment of the present invention.
Figure 2A:
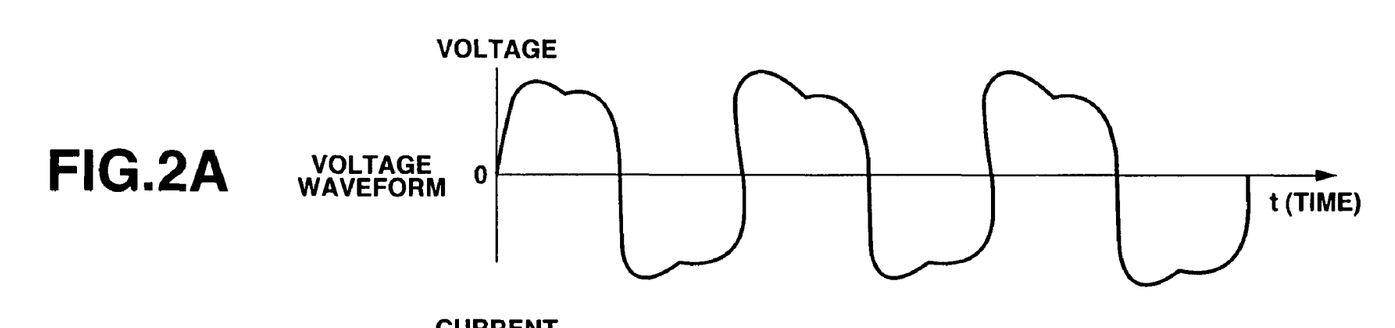
FIG. 2A is a voltage waveform diagram for describing an operation to be performed when a probe horizontally vibrates according to the first embodiment of the present invention.
Figure 2B:
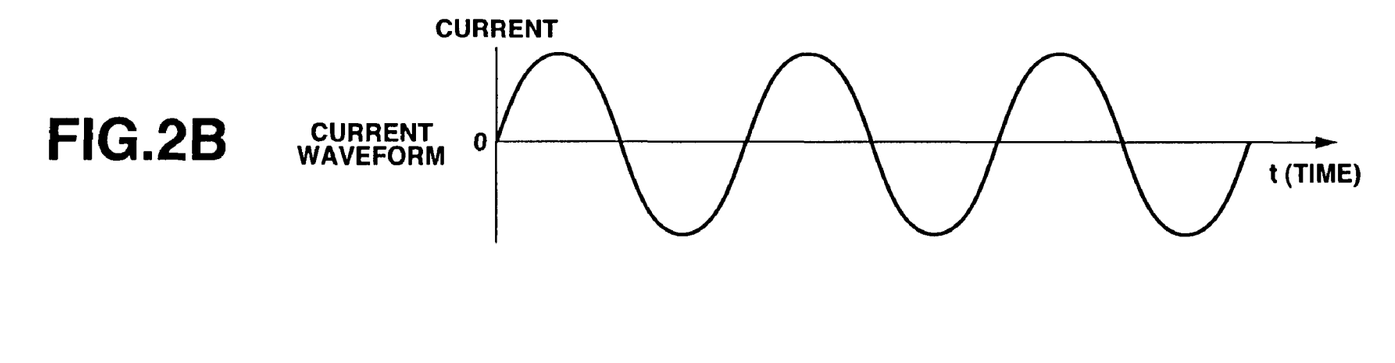
FIG. 2B is a current waveform diagram for describing an operation to be performed when the probe horizontally vibrates according to the first embodiment of the present invention.
Figure 3A:
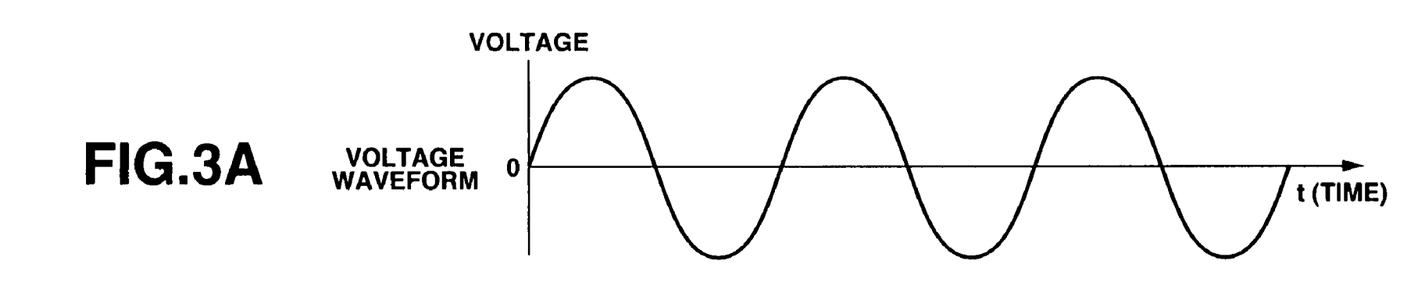
FIG. 3A is a voltage waveform diagram for describing an operation to be performed when the probe is normal according to the first embodiment of the present invention.
Figure 3B:
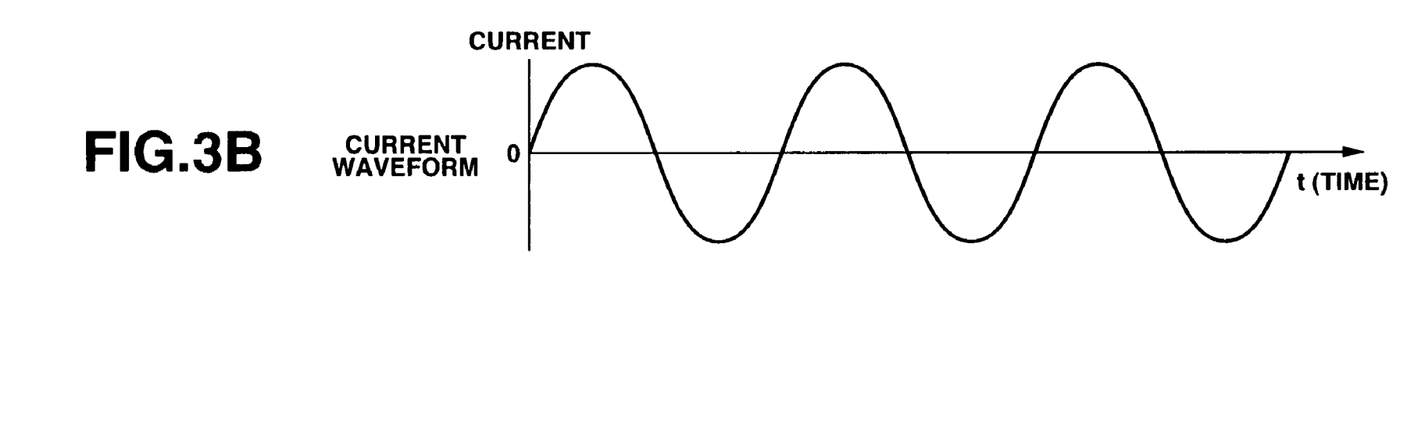
FIG. 3B is a current waveform diagram for describing an operation to be performed when the probe is normal according to the first embodiment of the present invention.
Figure 4:
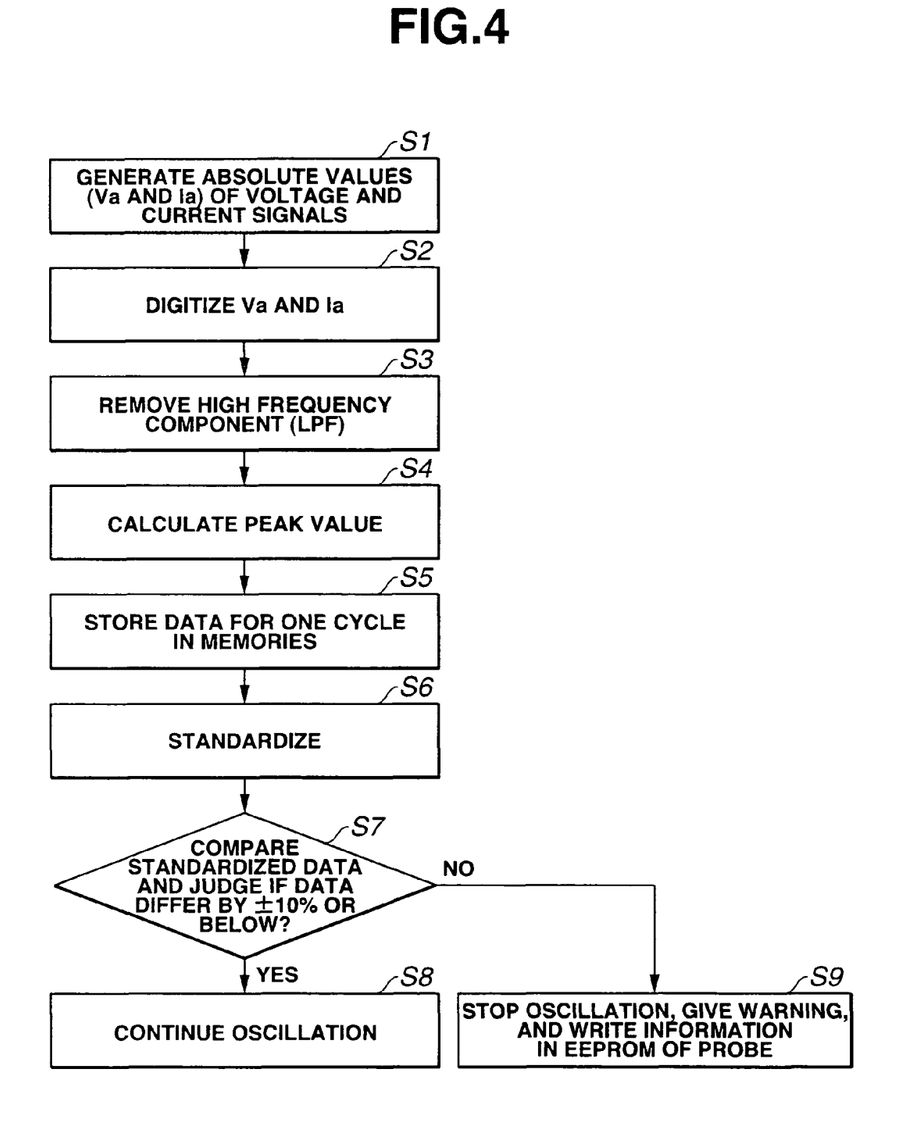
FIG. 4 is a flowchart for describing an operation of the ultrasonic surgical apparatus according to the first embodiment of the present invention.

FIGS. 1 to 4 relate to a first embodiment of the present invention; FIG. 1 is a block diagram showing a configuration of an ultrasonic surgical apparatus; FIG. 2 is an explanatory diagram for describing an operation to be performed when a probe has horizontally vibrated; FIG. 3 is an explanatory diagram for describing an operation to be performed when the probe is normal; and FIG. 4 is a flowchart for describing an operation of the ultrasonic surgical apparatus.

[Construction]

As shown in FIG. 1, an ultrasonic surgical apparatus 1 includes an ultrasonic driver 2 and a hand piece 3. The hand piece 3 is removably attached to the ultrasonic driver 2.

The ultrasonic driver 2 includes a CPU 4, a panel 5, a PLL circuit 20 and a horizontal vibration detecting circuit 30.

The hand piece 3 includes a connector 11, a case 12, an ultrasonic vibrator 13, a probe 14 and an electrically erasable programmable read-only memory (EEPROM) 15.

The case 12 accommodates the ultrasonic vibrator 13. The probe 14 is removably attached to the ultrasonic vibrator 13.

The probe 14 self-contains the EEPROM 15 as a memory.

The phase-locked loop (called PLL circuit hereinafter) 20 includes a digital oscillator (called DDS hereinafter) 21, an amplifier (called AMP hereinafter) 22, a detecting circuit 23, a rectangular wave generating circuit 24, a phase comparing circuit 25 and a U/D counter 26.

The horizontal vibration detecting circuit 30 includes an absolute value generating circuit 31, analog/digital converting circuits (called A/D converting circuits hereinafter) 32 and 33, low-pass filters (called LPFs hereinafter) 34 and 35, a V-memory 36, an I-memory 37, a peak value (called P-value) detecting circuit 38, a standardizing circuit 39, a comparing circuit 40 and a communication circuit 41.

The ultrasonic driver 2 generates a drive signal SIN by using the DDS 21 in order to ultrasonically vibrate the probe 14 fastened to the ultrasonic vibrator 13.

The AMP 22 amplifies the drive signal SIN output by the DDS 21 so as to supply the drive signal SIN to the ultrasonic vibrator 13 through the connector 11.

The detecting circuit 23 detects a current and voltage of an ultrasonic signal to be supplied to the ultrasonic vibrator 13 through the connector 11.

In order to generate phase signals of the voltage and current to be supplied to the ultrasonic vibrator 13, the rectangular wave generating circuit 24 generates rectangular waves for a voltage signal V and current signal I, which are detect signals from the detecting circuit 23 and outputs rectangular wave signals Vz and Iz for the voltage and current.

The phase comparing circuit 25 compares the rectangular wave signals Vz and Iz from the rectangular wave generating circuit 24 and generates an UP/DOWN signal of the phase difference.

In response to the UP/DOWN signal generated by the phase comparing circuit 25, the U/D counter 26 calculates a set frequency Fs of the drive signal to be supplied to the ultrasonic vibrator 13 based on an initial set frequency $F_0$, which is a frequency set in the beginning of PLL control and which is sent from the CPU 4.

The initial set frequency $F_o$ is stored as resonance frequency data of the probe 14 in advance in the EEPROM 15 provided within the probe 14. Data is read/written from/in the EEPROM 15 by the communication circuit 41.

These are the components relating to the PLL control of the ultrasonic driver 2.

The horizontal vibration detecting circuit 30 will be described below which is a component relating to the detection of a horizontal vibration of the probe 14 of the ultrasonic driver 2.

In the horizontal vibration detecting circuit 30, the absolute value generating circuit 31 generates absolute values of a voltage signal V and current signal I detected by the detecting circuit 23 and outputs absolute value signals Va and Ia thereof.

The A/D converting circuits 32 and 33 A/D convert the absolute value signals Va and Ia of the voltage and current, respectively to 8-bit digital signals Vd and Id, respectively.

The LPFs 34 and 35 are digital filters for removing high frequency noise of the digital signals Vd and Id.

According to the first embodiment, the LPFs 34 and 35 are digital filters but are not limited thereto. The same result can be obtained by providing an analog LPF between the detecting circuit 23 and the absolute value generating circuit 31. Alternatively, instead of an LPF, a band pass filter (BPF) may be used.

The V-memory 36 stores waveform data for a half cycle (or for one cycle) of the voltage represented by the digital signal Vd from the LPF 34 and outputs voltage waveform data Vm to the standardizing circuit 39.

The I-memory 37 stores waveform data for a half cycle (or for one cycle) of the current represented by the digital signal Id from the LPF 35 and outputs current waveform data Im to the standardizing circuit 39.

The P-value detecting circuit 38 detects a peak value Vpp of the voltage waveform data Vm from the LPF 34 and detects a peak value Ipp of the current waveform data Im from the LPF 35.

The standardizing circuit 39 standardizes voltage and current waveforms by using following equations EQ1 and EQ2:

Vs (standardized voltage signal)=*Vm* (voltage data for a half cycle or one cycle within the V-memory)/*Vpp* (voltage peak value)  EQ1

Is (standardized current signal)=*Im* (current data for a half cycle or one cycle within the I-memory)/*Ipp* (current peak value)  EQ2

(where the peak value is 1 in the V-memory and I-memory).

The comparing circuit 40 compares the voltage signal Vs and current signal Is standardized by the standardizing circuit 39 and detects whether the difference fits in a predetermined range, such as within ±10%, or not.

If the difference between the voltage signal Vs and the current signal Is is within ±10%, the comparing circuit 40 determines that the probe 14 is not horizontally vibrating. Then, the supply of voltage and current to the ultrasonic vibrator 13 is continued, and the ultrasonic vibrator 13 is caused to continue the ultrasonic driving.

If a predetermined number or more of waveforms having a difference over ±10% between the voltage signal Vs and the current signal Is occur (for example, if 20 waveforms having the difference over ±10% occur continuously), the comparing circuit 40 determines that the probe 14 is horizontally vibrating. Then, the comparing circuit 40 sends a signal TRANS indicating the occurrence to the CPU 4 and the communication circuit 41.

In response to the signal TRANS indicating the occurrence of the horizontal vibrations, the CPU 4 causes the DDS 21 to terminate the outputs of the SIN waveforms and causes the AMP circuit 6 to terminate the amplification. Furthermore, the CPU 4 causes the panel 5 to display a warning regarding the occurrence of horizontal vibrations. Thus, the CPU 4 can give a warning to a user.

The communication circuit 41 writes a signal indicating that the probe 14 is vibrating horizontally in the EEPROM 15 within the probe 14. Next, when the probe 14 is connected to the ultrasonic driver 2 through the ultrasonic vibrator 13, the communication circuit 41 gives a warning to a user upon the connection.

With this configuration, the ultrasonic vibrator 13 can generate ultrasonic vibrations.

The probe 14 is connected to the ultrasonic vibrator 13 and can transmit the ultrasonic vibrations to a living body tissue.

The PLL circuit 20 is drive signal generating means which can generate a drive signal for driving the ultrasonic vibrator 13.

The P-value detecting circuit 38 is peak detecting means which can detect the voltage peak value and current peak value of the drive signal supplied from the PLL circuit 20 to the ultrasonic vibrator 13.

The standardizing circuit 39 is drive signal standardizing means for standardizing voltage information and current information of the drive signal based on the result from the P-value detecting circuit 38.

The comparing circuit 40 is comparing means for comparing the voltage information standardized by the standardizing circuit 39 and the current information standardized by the standardizing circuit 39.

The CPU 4 is probe abnormality identifying means for identifying an abnormality of the probe 14 based on the comparison result from the comparing circuit 40.

The P-value detecting circuit 38, standardizing circuit 39 and comparing circuit 40 are included in drive signal distortion detecting means which can detect a waveform distortion of the drive signal to be supplied from the PLL circuit 20 to the ultrasonic vibrator 13.

[Operation]

FIG. 2A shows voltage waveforms caused when horizontal vibrations occur. FIG. 2B shows current waveforms caused when horizontal vibrations occur. FIG. 3A shows voltage waveforms caused when horizontal vibrations do not occur. FIG. 3B shows current waveforms caused when horizontal vibrations do not occur.

That is, when the probe 14 horizontally vibrates, the voltage waveforms are distorted as shown in FIG. 2A. According to the first embodiment, the horizontal vibrations are detected by standardizing the peak values of the voltage waveforms and current waveforms and comparing the waveforms.

As shown in FIG. 2B, when horizontal vibrations occur, the current waveforms are not distorted like the voltage waveforms and current waveforms caused when horizontal vibrations do not occur as shown in FIGS. 3A and 3B.

Next, a processing flow relating to the detection of the horizontal vibrations according to the first embodiment will be described with reference to FIG. 4.

First of all, at a step S1, the absolute value generating circuit 31 generates absolute values of a voltage signal V and current signal I from the detecting circuit 23.

Next, at a step S2, the A/D converting circuits 32 and 33 digitize the absolute value signals Va and Ia of the voltage and current from the absolute value generating circuit 31 and outputs digital signals Vd and Id.

Next, at a step S3, the LPFs 34 and 35 allows the passage of the voltage and current digital signals Vd and Id therethrough, and high frequency noise is removed.

Next, at a step S4, the P-value detecting circuit 38 calculates peak values within one cycle of the voltage and current digital signals having passed through the LPFs 34 and 35.

Next, at a step S5, the V-memory 36 and the I-memory 37 store data of voltage and current signals for one cycle.

Next, at a step S6, the standardizing circuit 39 standardizes the data stored in the V-memory 36 and I-memory 37 at the step S5 by using the peak values detected at the step S4.

Next, at a step S7, the comparing circuit 40 compares the data standardized at the step S6.

If the comparison result at the step S7 indicates that a predetermined number or more of waveforms having a difference over ±10% occur, the CPU 4 determines that horizontal vibrations are occurring and gives a warning by using the panel 5 at a step S9. Furthermore, at the step S9, the ultrasonic vibrator 13 is caused to terminate the oscillation, and the communication circuit 41 writes information that horizontal vibrations are occurring in the EEPROM 15 within the probe 14.

If the comparison result at the step S7 indicates that the difference is within ±10%, the CPU 4 causes the ultrasonic vibrator 13 to continue the oscillation at a step S8.

In other words, if predetermined number or more of waveforms having the difference over ±10% between the standardized voltage signal and current signal occur, the CPU 4 inhibits the voltage and current supply to the ultrasonic vibrator 13. Then, the CPU 4 determines that horizontal vibrations is occurring and gives a warning by using the panel 5.

[Advantages]

According to the first embodiment, by detecting distortions in waveforms of voltage signals, the horizontal vibrations of the probe 14 are detected. Thus, the horizontal vibrations of the probe 14 can be detected with extremely high accuracy, and the ability for finding an abnormal operation of the probe 14 can be improved.

Second Embodiment

Figure 5:
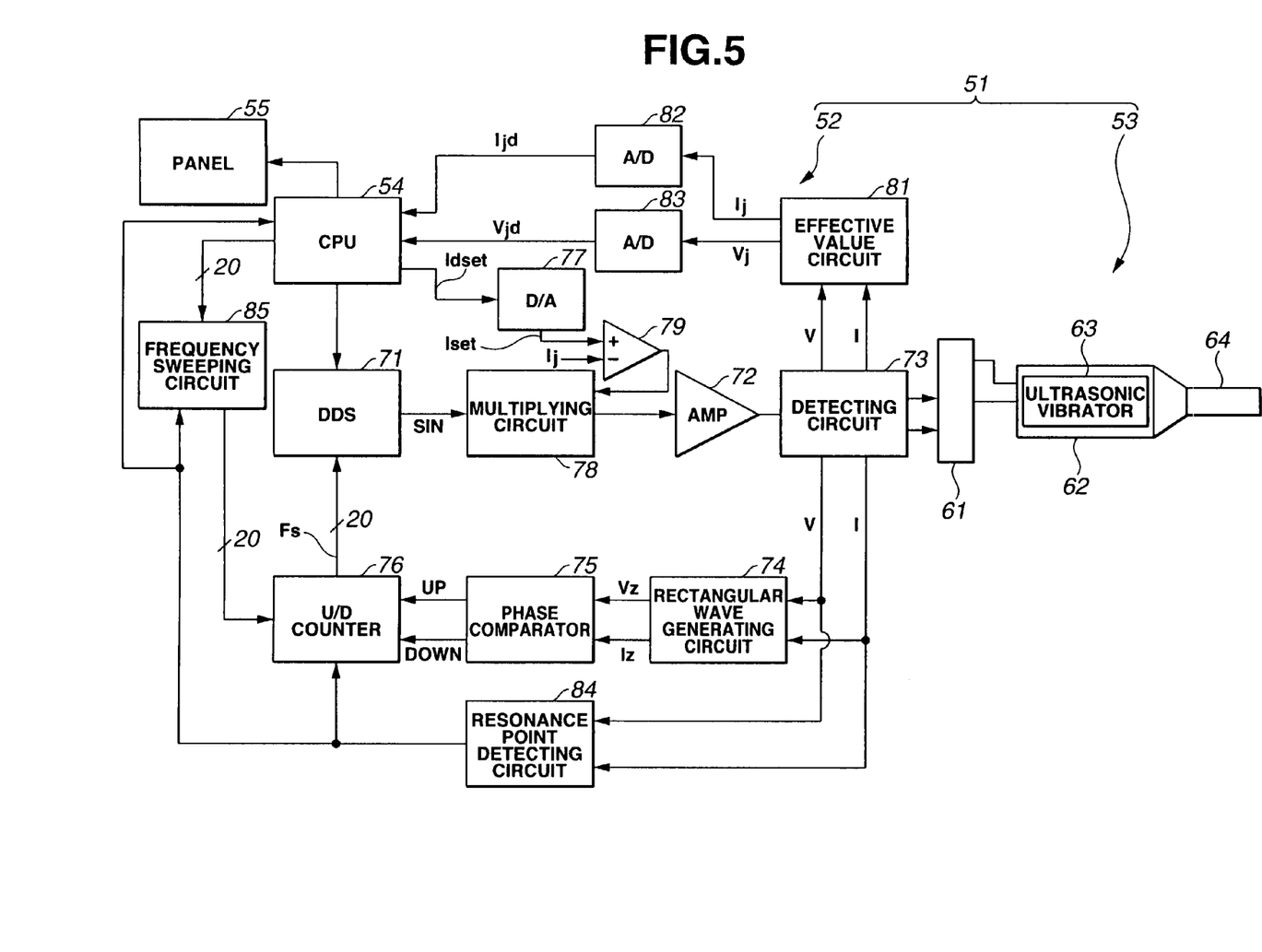
FIG. 5 is a block diagram illustrating a configuration of an ultrasonic surgical apparatus according to a second embodiment of the present invention.
Figure 6A:
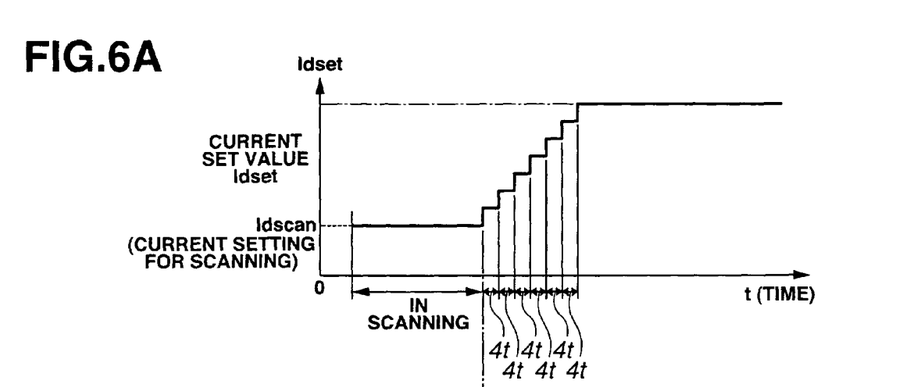
FIG. 6A is a diagram for describing changes in current set value according to the second embodiment of the present invention.
Figure 6B:
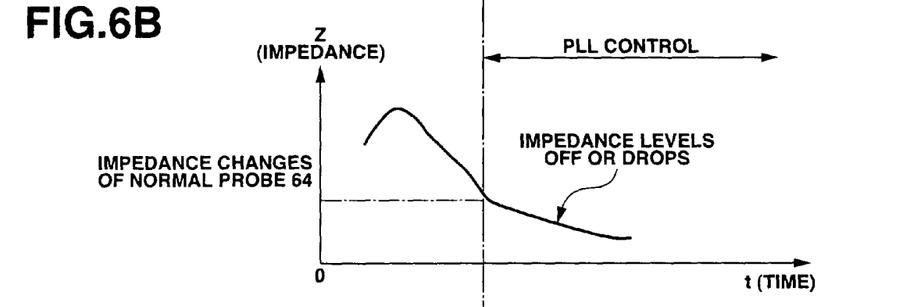
FIG. 6B is an explanatory diagram for describing impedance of a normal probe according to the second embodiment of the present invention.
Figure 6C:
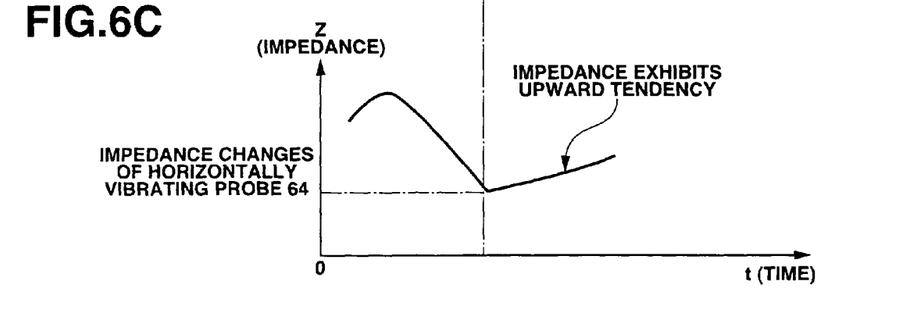
FIG. 6C is an explanatory diagram for describing an impedance of a horizontally vibrating probe according to the second embodiment of the present invention.
Figure 7:
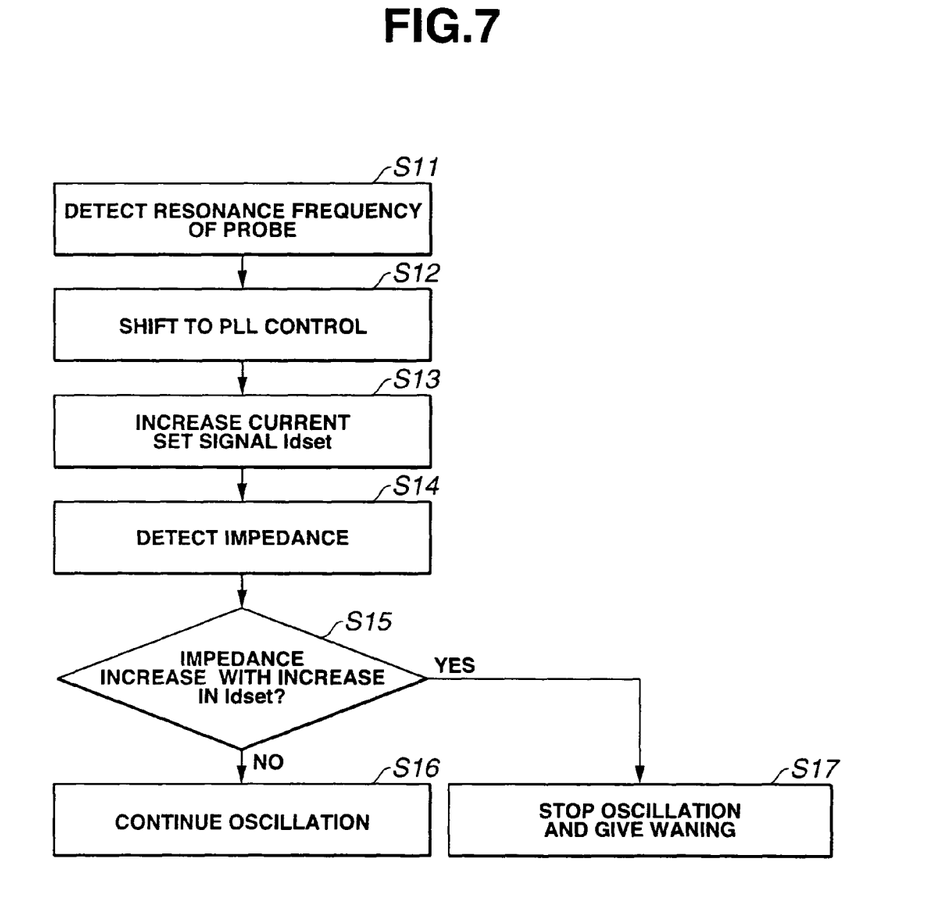
FIG. 7 is a flowchart for describing an operation of the ultrasonic surgical apparatus according to the second embodiment of the present invention.

FIGS. 5 to 7 relate to a second embodiment of the present invention; FIG. 5 is a block diagram showing a configuration of an ultrasonic surgical apparatus; FIGS. 6A to 6C are explanatory diagrams for describing impedance monitoring of an ultrasonic vibrator; and FIG. 7 is a flowchart for describing an operation of the ultrasonic surgical apparatus.

[Construction]

According to the first embodiment shown in FIGS. 1 to 4, voltage, and current waveforms are standardized and voltage and current waveforms are compared so that the occurrence of horizontal vibrations can be detected. On the other hand, according to the second embodiment shown in FIG. 5, changes in impedance in accordance with a current set value is monitored so as to detect horizontal vibrations.

As shown in FIG. 5, an ultrasonic surgical apparatus 51 includes an ultrasonic driver 52 and a hand piece 53. The hand piece 53 is removably attached to the ultrasonic driver 52.

The ultrasonic driver 52 includes a CPU 54, a panel 55, a DDS 71, an AMP 72, a detecting circuit 73, a rectangular wave generating circuit 74, a phase comparing circuit 75, a U/D counter 76, an analog/digital converting circuit (called D/A converting circuit hereinafter) 77, a multiplying circuit 78, a differential amplifier 79, an effective value generating circuit 81, A/D converting circuits 82 and 83, a resonance point detecting circuit 84 and a frequency sweeping circuit 85.

The hand piece 53 includes a connector 61, a case 62, an ultrasonic vibrator 63 and a probe 64.

The case 62 accommodates the ultrasonic vibrator 63. The probe 64 is removably attached to the ultrasonic vibrator 63.

The configuration relating to a PLL operation by the DDS 71, AMP 72, detecting circuit 73, rectangular wave generating circuit 74, phase comparing circuit 75 and U/D counter 76 is the same as the one according to the first embodiment.

According to the first embodiment shown in FIG. 1, the probe 14 contains the EEPROM 15 which stores signals representing resonance frequencies and horizontal vibrations. On the other hand, according to the second embodiment shown in FIG. 5, the probe 64 does not self-contain an EEPROM but the resonance point detecting circuit 84 is provided in the ultrasonic driver 52 as a circuit for detecting oscillations of resonance frequencies of the probe 64, which is different from the first embodiment.

The frequency sweeping circuit 85 sweeps frequencies in a predetermined frequency range in accordance with a command from the CPU 54. The frequency sweeping circuit 85 terminates the operation of the U/D counter 76 during the frequency sweeping.

The resonance point detecting circuit 84 detects resonance frequencies of the probe 64 during the frequency sweeping. When a resonance frequency is detected, the resonance point detecting circuit 84 terminates the sweeping by the frequency sweeping circuit 85, starts the operation of the U/D counter 76 and starts a PLL operation.

During the detection of resonance frequencies, the CPU 54 decreases the current setting Idset and increases the set current Idset in stages after the shift to the PLL operation.

The set current Idset output from the CPU 54 is converted to an analog signal Iset by the D/A converting circuit 77, and the differential amplifier 79 performs a differential amplification on the analog signal Iset with respect to a current value Ij. Then, the result is multiplied, by the multiplier 78, by a drive signal SIN output by the DDS 71.

The detection of horizontal vibrations according to the second embodiment will be described.

The effective value generating circuit 81 generates effective values of the voltage signal V and current signal I detected by the detecting circuit 73.

The effective value voltage signal Vj and current signal Ij generated by the effective value generating circuit 81 are A/D-converted by the A/D converting circuits 82 and 83, respectively, and are captured into the CPU 54 as digitized voltage signal Vjd and current signal Ijd.

While the current set value signal Idset is increased gradually in stages after the detection of the resonance frequency, the CPU 54 monitors the impedance at each set current.

Under this construction, the DDS 71, AMP 72, detecting circuit 73, rectangular wave generating circuit 74, a phase comparing circuit 75 and U/D counter 76 are included in drive signal generating means which can generate a drive signal for driving the ultrasonic vibrator 63.

The CPU 54, D/A converting circuit 77, multiplying circuit 78 and differential amplifier 79 are included in current setting means for setting a current to be supplied to the ultrasonic vibrator 63.

The resonance point detecting circuit 84 is resonance point detecting means for detecting a resonance frequency of the probe 64.

The CPU 54 is PLL controlling means which shifts to PLL control after the resonance frequency is detected.

The CPU 54, effective value generating circuit 81 and A/D converting circuits 82 and 83 are included in impedance measuring means for measuring impedance relating to the ultrasonic vibrator 63 from voltage and current signals supplied to the ultrasonic vibrator 63.

The CPU 54 is current controlling means for increasing current to be supplied to the ultrasonic vibrator 63 in stages after the shift to the PLL control.

Furthermore, when the current to be supplied is increased in stages, the CPU 54 uses the impedance measuring means to measure impedance relating to the ultrasonic vibrator 63 and identifies whether or not the probe 64 is horizontally vibrating based on a change in the impedance.

The resonance point detecting circuit 84 is resonance point detecting means which can detect a resonance point of the ultrasonic vibrator 63 connecting to the probe 64 by changing the frequency of the drive signal to be supplied from the drive signal generating means to the ultrasonic vibrator 63.

The CPU 54 is also resonance point tracking and controlling means which starts a control operation on the drive signal generating means so that the resonant point can be tracked and be controlled when the resonance point detecting circuit 84 detects the resonance point.

The CPU 54, D/A converting circuit 77, multiplying circuit 78 and differential amplifier 79 are included in drive current setting means which can set a current value of the drive signal.

The CPU 54 is current controlling means for increasing in stages and controlling the current of the drive signal based on the current set value set by the drive current setting means after the resonance point tracking and controlling means starts a control operation.

The effective value generating circuit 81 and A/D converting circuits 82 and 83 are included in impedance monitoring means for monitoring impedance changes of the ultrasonic vibrator 63 based on the drive signal for increasing in stages and supplying a current by the current controlling means.

Also, the CPU 54 is horizontal vibration occurrence discriminating means for discriminating whether or not the probe 64 is horizontally vibrating based on a monitoring result from screen impedance monitoring means.

[Operation]

FIG. 6A shows changes in current set value Idset by the CPU 54; FIG. 6B shows changes in impedance of the normal probe 64; and FIG. 6C shows changes in impedance of the probe 64 having horizontal vibrations.

The normal probe 64 shown in FIG. 6B has impedance values leveling off or decreasing with an increase in current setting shown in FIG. 6A after the detection of a resonance frequency at a time T1.

However, the probe 64 having horizontal vibrations shown in FIG. 6C has impedance values increasing with increases in current setting shown in FIG. 6A.

This is based on the fact that horizontal vibrations do not occur at lower current setting but occur at higher current setting.

When the impedance values of the probe 64 have an upward tendency with increases in current setting, the CPU 54 determines that horizontal vibrations have occurred in the probe 64 and terminates the output of ultrasound (or terminates the output of drive waveforms). Furthermore, the CPU 54 displays on the panel 55 the fact that horizontal vibrations have occurred and gives a warning to a user by generating an audible alarm.

Next, a processing flow relating to the detection of horizontal vibrations according to the second embodiment will be described with reference to FIG. 7.

First of all, at a step S11, the resonance point detecting circuit 84 detects a resonance frequency of the probe 64.

Next, at a step S12, in response to the detection of the resonance frequency by the resonance point detecting circuit 84 at the step S11, the CPU 54 causes the resonance point detecting circuit 84 to terminate the detection of the resonance frequency and shifts to a PLL operation.

Next, at a step S13, the CPU 54 identifies the shift to the PLL operation and increases the set value of current to be supplied to the ultrasonic vibrator 63.

Next, at a step S14, the CPU 54 detects an impedance change while increasing the current setting based on the digitized voltage signal Vjd and current signal Ijd.

Next, at a step S15, the CPU 54 determines whether or not the impedance changes detected at the step S14 tend to increase.

If it is determined at the step S15 that the impedance changes decrease or level off, the CPU 54 controls the probe 64 to continue ultrasonic oscillation at a step S16.

If it is determined at the step S15 that the impedance changes tend to increase, the CPU 54 determines, at a step S17, that horizontal vibrations are occurring and gives a warning. Then, the CPU 54 terminates the output of ultrasounds.

[Advantages]

According to the second embodiment, in addition to the same advantages as those of the first embodiment, the current setting is increased little by little (by Δt) in stages after PLL control. Thus, the damages on the ultrasonic vibrator 63 can be prevented, and a circuit configuration and method for detecting horizontal vibrations can be obtained extremely easily.

The invention being thus described, it will be obvious that the same may be varied in many ways. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. An abnormality detecting method for an ultrasonic surgical apparatus including an ultrasonic vibrator which can generate ultrasonic vibrations and a probe which is connected to the ultrasonic vibrator and can transmit the ultrasonic vibrations, the method comprising the steps of:
   generating a drive signal for driving the ultrasonic vibrator;
   detecting a voltage signal and a current signal to be supplied to the ultrasonic vibrator based on the drive signal;
   storing voltage data for a half cycle or one cycle of the voltage signal and current data for a half cycle or one cycle of the current signal;

comparing a voltage waveform represented by the voltage data for the half cycle or the one cycle of the voltage signal and a current waveform represented by the current data for the half cycle or the one cycle of the current signal and detecting a waveform distortion of the drive signal to be supplied to the ultrasonic vibrator; and identifying that the probe has an abnormality in accordance with whether or not a difference between the voltage waveform and the current waveform fits in a predetermined range.

2. The abnormality detecting method according to claim 1, wherein the detection of the abnormality of the probe is a detection of horizontal vibrations occurring in the probe.

3. The abnormality detecting method according to claim 1, wherein the detection of horizontal vibrations is performed by detecting a current peak value and a voltage peak value of the drive signal and comparing a voltage waveform and current waveform which are standardized based on a result of the detection.

4. The abnormality detecting method according to claim 1, further comprising a step of stopping supplying the drive signal to the ultrasonic vibrator when it is identified that the probe has an abnormality.

5. The abnormality detecting method according to claim 1, wherein a warning indicating that an abnormality as occurred in the probe is displayed on a panel when it is identified that the probe has an abnormality.

* * * * *